United States Patent [19]

Marquis et al.

[11] Patent Number: 5,283,356
[45] Date of Patent: Feb. 1, 1994

[54] PROCESS FOR MANUFACTURING ALKYLENE CARBONATES USING METAL PHTHALOCYANINE CATALYSTS

[75] Inventors: Edward T. Marquis, Austin; John R. Sanderson, Leander, both of Tex.

[73] Assignee: Texaco Chemical Company, White Plains, N.Y.

[21] Appl. No.: 923,760

[22] Filed: Aug. 3, 1992

[51] Int. Cl.$^5$ ............................................. C07C 69/96
[52] U.S. Cl. .................................. 558/260; 558/275; 558/277; 549/230
[58] Field of Search ..................... 558/277; 549/230

[56] References Cited

U.S. PATENT DOCUMENTS

| | | | |
|---|---|---|---|
| 2,766,258 | 10/1956 | Malkemus | 549/230 |
| 2,773,070 | 12/1956 | Lichtwenwalter | 549/230 |
| 2,873,282 | 2/1959 | McClellan | 549/230 |
| 4,009,183 | 2/1977 | Fumagalli et al. | 549/230 |
| 4,233,221 | 11/1980 | Raines et al. | 549/230 |
| 4,663,467 | 5/1987 | Kruper et al. | 549/230 |
| 4,783,445 | 11/1988 | Sun | 502/170 |
| 4,786,741 | 11/1988 | Sachs | 549/230 |
| 4,824,969 | 4/1989 | Austin et al. | 549/230 |
| 4,892,954 | 1/1990 | Brindöpke et al. | 549/229 |
| 4,912,267 | 3/1990 | Sanderson et al. | 568/909.8 |
| 4,981,948 | 1/1991 | Kawachi et al. | 528/405 |

FOREIGN PATENT DOCUMENTS 0297647 6/1988 European Pat. Off. .
63-181765 7/1988 Japan .
760966 11/1956 United Kingdom .

OTHER PUBLICATIONS

W. J. Peppel, "Preparation and Properties of the Alkylene Carbonates," *Industrial and Engineering Chemistry*, vol. 50, No. 5, pp. 767-770 (May 1958).

Buysch, "Carbon Acid Esters," *Ullmann's Encyclopedia of Industrial Chemistry*, vol. A5, pp. 197-201 (1986).

"Carbonic and Chloroformic Esters," *Kirk-Othmer Encyclopedia of Chemical Technology*, 3rd Edition, pp. 766-770 (1979).

*Primary Examiner*—Paul J. Killos
*Assistant Examiner*—Dwayne C. Jones
*Attorney, Agent, or Firm*—Kenneth R. Priem; James L. Bailey; Russell R. Stolle

[57] ABSTRACT

A method for the manufacture of alkylene carbonates is disclosed. Alkylene carbonates are prepared by reacting alkylene oxides and carbon dioxide in the presence of a metal phthalocyanine catalyst.

18 Claims, No Drawings

PROCESS FOR MANUFACTURING ALKYLENE CARBONATES USING METAL PHTHALOCYANINE CATALYSTS

BACKGROUND OF THE INVENTION

1. Field of the Invention

The invention relates to the preparation of alkylene carbonates, also known as glycol carbonates, by reaction of alkylene oxides with carbon dioxide, and more particularly to such processes in which catalysts are employed.

2. Description of Related Methods

The reaction of alkylene oxides with carbon dioxide in the presence of a catalyst is known. U.S. Pat. 2,773,070 to Lichtenwalter et al. discloses a process for preparing alkylene carbonates using an ammonium halide catalyst. U.S. Pat. No. 2,873,282 to Mc Clellan discloses the use of certain quaternary ammonium compounds to catalyze the reaction of alkylene oxides and carbon dioxide. W. J. Peppel, in "Preparation and Properties of the Alkylene Carbonates,"*Industrial and Engineering Chemistry*, vol. 50, no. 5, pp. 767-770 (May 1958), provides an overview of the various methods then known for the preparation of alkylene carbonates.

It appears that most of the known processes employ halogen-based catalysts. For example, U.S. Pat. No. 4,786,741 to Sachs teaches a process for preparing alkylene carbonates that employs a catalyst selected from the group consisting of organic quaternary ammonium halides organic quaternary phosphonium halides, organic sulfonium halides, and organic antimony halides. European Patent Application 0 297 647 claims a process wherein alkylene carbonates are prepared using a catalyst comprising an alkali or alkaline earth metal halide. Japanese Patent Application Number 63-181765 also discloses a method for the preparation of alkylene carbonates using an alkali halide catalyst. Halide-based catalysts, however, tend to contaminate the alkylene carbonate product with halogen compounds. Other known catalysts may include a strong base that deactivates or decomposes the carbonate, or that causes the epoxide to react with epoxide rather than with carbon dioxide.

Applicants have discovered that metal phthalocyanine salts provide good yields of alkylene carbonates. Applicants have further discovered that it is possible to obtain good yields using non-halogenated metal phthalocyanine salts, and thereby avoid contaminating the alkylene carbonate product with halogen compounds.

SUMMARY OF THE INVENTION

The invention concerns a process for the manufacture of alkylene carbonates, comprising reacting (a) alkylene oxide having the formula:

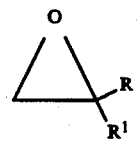

in which R is hydrogen and $R^1$ is selected from the group consisting of hydrogen, aryl groups having from 6 to 20 carbon atoms, alkyl groups containing from 1 to 20 carbon atoms, cycloalkyl groups containing from 5 to 20 carbon atoms, and alkenyl groups containing from 2 to 20 carbon atoms with (b) carbon dioxide, in the presence of a catalytically effective amount of a metal phthalocyanine. The invention also concerns a process for preparing alkylene carbonates, comprising reacting (a) alkylene oxide having the formula:

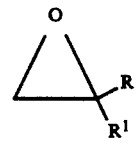

in which R is hydrogen and $R^1$ is selected from the group consisting of hydrogen, alkyl groups containing from 1 to 5 carbon atoms, and alkenyl groups containing from 2 to 5 carbon atoms with (b) a molar excess of carbon dioxide, at a temperature of from about 100° to about 225° C. and in the presence of a catalytically effective amount of a non-halogenated metal phthalocyanine. The invention further concerns a process for preparing alkylene carbonates, comprising reacting (a) alkylene oxide having the formula:

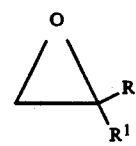

in which R is hydrogen and $R^1$ is selected from the group consisting of hydrogen and alkyl groups containing from 1 to 5 carbon atoms with (b) a molar excess of carbon dioxide, at a temperature of from about 175° to about 215° C. and in the presence of a catalytically effective amount of chromium phthalocyanine.

DESCRIPTION OF THE PREFERRED EMBODIMENTS

Alkylene oxides that may be employed in the reaction of the present invention include those of the oxirane system. Preferably the alkylene oxide has the following structural formula:

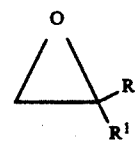

in which R and $R^1$ may be selected from the group consisting of hydrogen, aryl groups having from 6 to about 20 carbon atoms, alkyl groups containing from to about 20 carbon atoms, cycloalkyl groups containing from 5 to about 20 carbon atoms, and alkenyl groups containing from 2 to about 20 carbon atoms. Preferably, R is hydrogen and $R^1$ is selected from the group consisting of hydrogen, aryl groups having from 6 to about 12 carbon atoms, alkyl groups containing from 1 to about 5 carbon atoms, cycloalkyl groups containing from 5 to about 12 carbon atoms, and alkenyl groups containing from 2 to about 5 carbon atoms. More preferably, R is hydrogen and $R^1$ is selected from the group consisting of hydrogen, alkyl groups containing from 1 to about 5 carbon atoms, and alkenyl groups containing from 2 to about 5 carbon atoms. Especially preferred are ethylene oxide and propylene oxide The oxirane compounds, as shown by the formula above, have the ring oxygen atom attached to two adjacent carbon atoms.

The reaction may be carried out at a temperature of from about 100° to about 225° C. or higher, preferably from about 175° to about 215° C. The reaction may be carried out at atmospheric pressure or, preferably, under a pressure of about 300 psig or greater. More preferably, the reaction is carried out under a pressure of about 1000 to about 3000 psig. The reaction may be conducted either batch-wise or continuously.

In a continuous reaction, alkylene oxide and carbon dioxide are introduced to a continuous reactor containing the catalyst, from which a portion of the reaction mixture may be continuously recirculated through the reactor. Another portion of this reaction mixture is continuously withdrawn and flashed to remove unreacted carbon dioxide and alkylene oxide, which are compressed and returned to the reactor. The residue from the flashing treatment is subjected to distillation to separate the alkylene carbonate from the catalyst solution. Residual catalyst solution or slurry (bottoms) may be returned directly to the reactor. At times, it may be desirable to discard a portion of the recovered catalyst stream to prevent accumulation of unwanted by-products in the catalyst stream.

Alternatively, batches of alkylene oxide and catalyst may be introduced into an autoclave or kettle type reactor. The desired pressure may be built up by introducing carbon dioxide. Typically, the reaction mixture is heated to reaction temperature, agitated, and held under a superatmospheric pressure of carbon dioxide.

The alkylene oxide and carbon dioxide should be mixed in proportion to provide an excess of carbon dioxide over and above the stoichiometric amount required for reaction. This excess may be on the order of from about 1.1 moles of carbon dioxide per mole of alkylene oxide to about 10 moles of carbon dioxide per mole of alkylene oxide. An excess of alkylene oxide should be avoided, because it results in undesired by-products, chiefly alkylene oxide polymers, and because explosive conditions may result.

Catalysts useful in the present invention are metal phthalocyanines. Phthalocyanine may be represented by the following formula:

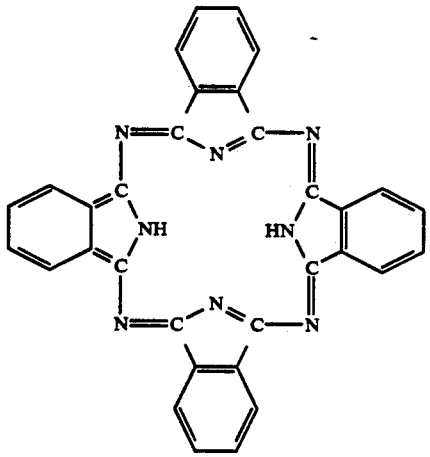

The two hydrogen atoms in the center of the phthalocyanine molecule may be replaced by a metal, giving a metal phthalocyanine, as depicted below:

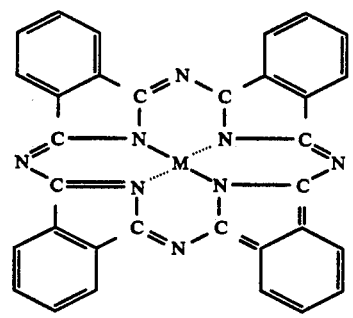

M = Metal

The metal component of the metal phthalocyanine may be in a high oxidation state, or in a lower oxidation state. For example, Ferric ($Fe+++$) or Ferrous ($Fe++$) may be substituted for the two hydrogen atoms. Additionally, from 1 to 16 of the peripheral hydrogen atoms of the four benzene rings of the molecule may be replaced by various organic and inorganic groups.

The metal component of the metal phthalocyanine catalyst may be selected from the following: alkali metals, alkaline earth metals, transition metals, and main group metals. Preferably, the metal component of the metal phthalocyanine is selected from the transition metals of the Periodic Table, such as, for example, cobalt, copper, chromium, iron, manganese, nickel, titanium, vanadyl, and zirconium. An especially preferred catalyst is chromium phthalocyanine. Other suitable metal components of the metal phthalocyanine catalysts of the present inventive process include those of the main metal group, such as, for example, aluminum, cadmium, lead, tin, and zinc. Other metal phthalocyanines may be selected by those skilled in the art. However, to avoid the presence of halogen compounds in the alkylene carbonate products, non-halogenated metal phthalocyanines should be used. Metal phthalocyanines are commercially available from vendors, such as ROC/RIC Corp.

The amount of catalyst used should be from about 0.1% to about 10%, preferably from about 1% to about 5%, based on the weight of the reaction mixture In general, the greater the catalyst concentration, within these limits, the more rapid and complete the reaction.

The invention will be further illustrated by the following examples, which are given by way of illustration and not as limitations on the scope of this invention. The entire text of every patent, patent application or other reference mentioned above is hereby incorporated herein by reference.

EXAMPLES

Example 1

To a clean, dry, 1-liter 316 stainless steel autoclave were added 150.0 g of propylene oxide (2.58 moles) and 8.0 g of manganous phthalocyanine (from ROC/RIC Corp.) The autoclave was purged with carbon dioxide, and then 185.0 g (4.20 moles) of carbon dioxide were added at ambient temperature. The reaction mixture was stirred and heated to 180° C., and held at 180° C. for 2.0 hours while stirring, before cooling to ambient temperature. The liquid product weighed 175.8 g. After filtration, the weight of the filtrate weighed 153.7 g. Gas chromatography indicated the presence of 54.0% propylene carbonate in the filtrate (83.02 g propylene carbonate, or 0.8132 moles propylene carbonate). The yield of propylene carbonate was 31.5 %.

Example 2

In an experiment identical to Example ? above, except that 8.0 g of chromium phthalocyanine (from Comprehensive Research Corp.) was used as catalyst, the filtrate contained 91.80% propylene carbonate (199.2 g, 1.95 moles), for a 75.6 % yield of propylene carbonate.

Example 3

In an experiment identical to Example 1 above, except that 8.0 g of chloroferric phthalocyanine was used as catalyst, the filtrate contained 80.02 % propylene carbonate (153.0 g, 1.50 moles), for a 58.0% yield of propylene carbonate.

Examole 4

In an experiment identical to Example 1 above, except that 8.0 g of hydroxyaluminum phthalocyanine (from ROC/RIC Corp.) was used as catalyst, the filtrate contained 56.2% propylene carbonate (80.30 g, 0.79 moles), for a 30.46 % yield of propylene carbonate.

Example 5

In an experiment identical to Example 1 above, except that 8.0 g of chloroaluminum phthalocyanine (from ROC/RIC Corp.) was used as catalyst, the filtrate contained 98.44% propylene carbonate (229.9 g, 2.25 moles), for an 87.2 % yield of propylene carbonate.

We claim:

1. A process for the manufacture of alkylene carbonates, comprising reacting (a) alkylene oxide having the formula:

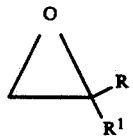

in which R is hydrogen and $R^1$ is selected from the group consisting of hydrogen, aryl groups having from 6 to 20 carbon atoms, alkyl groups containing from 1 to 20 carbon atoms, cycloalkyl groups containing from 5 to 20 carbon atoms, and alkenyl groups containing from 2 to 20 carbon atoms with (b) carbon dioxide, in the presence of a catalytically effective amount of a metal phthalocyanine.

2. The process of claim 1, wherein the metal of said metal phthalocyanine is selected from the transition metals of the Periodic Table.

3. The process of claim 1, wherein the metal of said metal phthalocyanine is selected from the group consisting of cobalt, copper, chromium, iron, manganese, nickel, titanium, vanadyl, and zirconium.

4. The process of claim 1, wherein the metal of said metal phthalocyanine is selected from the group consisting of aluminum, cadmium, lead, tin, and zinc.

5. The process of claim in which the metal phthalocyanine is selected from the group consisting of manganous phthalocyanine, chromium phthalocyanine, chloroferric phthalocyanine, hydroxyaluminum phthalocyanine, and chloroaluminum phthalocyanine.

6. The process of claim in which the metal phthalocyanine is selected from the group consisting of manganous phthalocyanine, chromium phthalocyanine, and hydroxyaluminum phthalocyanine.

7. The process of claim 1, in which the alkylene oxide and carbon dioxide are reacted at a temperature of from about 100° to about 225° C.

8. The process of claim 1, in which the alkylene oxide and carbon dioxide are reacted at a temperature of from about 175° to about 215° C. and at a pressure of from about 300 to about 2000 psig.

9. The process of claim in which the metal phthalocyanine is selected from the group consisting of chloroaluminum phthalocyanine and chromium phthalocyanine, and in which the alkylene oxide and carbon dioxide are reacted at a temperature of from about 175° to about 215° C and at a pressure greater than about 300 psig.

10. A process for preparing alkylene carbonates, comprising reacting (a) alkylene oxide having the formula:

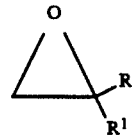

in which R is hydrogen and $R^1$ is selected from the group consisting of hydrogen, alkyl groups containing from 1 to 5 carbon atoms, and alkenyl groups containing from 2 to 5 carbon atoms with (b) a molar excess of carbon dioxide, at a temperature of from about 100° to about 225° C. and in the presence of a catalytically effective amount of a non-halogenated metal phthalocyanine.

11. The process of claim 10, wherein the metal of said metal phthalocyanine is selected from the transition metals of the Periodic Table.

12. The process of claim 10, wherein the metal of said metal phthalocyanine is selected from the group consisting of cobalt, copper, chromium, iron, manganese, nickel, titanium, vanadyl, and zirconium.

13. The process of claim 10, wherein the metal of said metal phthalocyanine is selected from the group consisting of aluminum, cadmium, lead, tin, and zinc.

14. The process of claim 10, in which the metal phthalocyanine is selected from the group consisting of manganous phthalocyanine, chromium phthalocyanine, and hydroxyaluminum phthalocyanine.

15. The process of claim 10, in which the alkylene oxide and carbon dioxide are reacted at a temperature of from about 175° to about 215° C. and at a pressure greater than about 300 psig.

16. The process of claim 10, in which the metal phthalocyanine is chromium phthalocyanine 17. A process for preparing alkylene carbonates, comprising reacting (a) alkylene oxide having the formula:

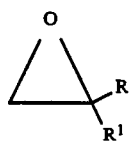

in which R is hydrogen and $R^1$ is selected from the group consisting of hydrogen and alkyl groups containing from 1 to 5 carbon atoms with (b) a molar excess of carbon dioxide, at a temperature of from about 175° to about 215° C. and in the presence of a catalytically effective amount of chromium phthalocyanine.

18. The process of claim 17, in which the alkylene oxide is selected from the group consisting of ethylene oxide and propylene oxide.